United States Patent
Steiner et al.

(10) Patent No.: US 6,613,205 B1
(45) Date of Patent: Sep. 2, 2003

(54) ELECTROCHEMICAL SENSOR

(75) Inventors: Gregor Steiner, Graz (AT); Bernhard Schaffar, Graz (AT); Marie-Luise Schinnerl, Semriach (AT); Christoph Ritter, Graz (AT)

(73) Assignee: F. Hoffmann-La Roche AG, Basel (CH)

(*) Notice: Subject to any disclaimer, the term of this patent is extended or adjusted under 35 U.S.C. 154(b) by 0 days.

(21) Appl. No.: 09/518,665

(22) Filed: Mar. 3, 2000

(30) Foreign Application Priority Data

Mar. 5, 1999 (EP) .............................. 99890077

(51) Int. Cl.⁷ ........................................... G01N 27/327
(52) U.S. Cl. ............................ 204/403.01; 204/403.15; 204/433
(58) Field of Search ................... 204/403, 433, 204/403.01, 403.15

(56) References Cited

U.S. PATENT DOCUMENTS

| | | | |
|---|---|---|---|
| 4,582,589 A | * 4/1986 | Ushizawa et al. | 204/433 |
| 4,613,422 A | 9/1986 | Lauks | |
| 4,739,380 A | 4/1988 | Lauks et al. | |
| 5,352,352 A | 10/1994 | Tsukada et al. | |
| 5,507,936 A | 4/1996 | Hatschek et al. | |
| 5,656,142 A | * 8/1997 | Park et al. | 204/403 |
| 5,707,502 A | * 1/1998 | McCaffrey et al. | 204/403 |
| 5,858,186 A | * 1/1999 | Glass | 204/403 |

FOREIGN PATENT DOCUMENTS

| | | |
|---|---|---|
| DE | 3840962 | 6/1990 |
| DE | 4430662 | 3/1996 |
| DE | 19506863 | 8/1996 |
| EP | 0190005 | 8/1986 |
| EP | 0603154 | 6/1994 |
| EP | 0651248 | 5/1995 |
| GB | 2289541 | 11/1995 |

OTHER PUBLICATIONS

Patent Abstracts of Japan, vol. D13, No. 351 (P–912), Aug. 7, 1989 of JP 01 112148, Terumo Corp.

Van der Spiegel et al., "The Extended Gate Chemically Sensitive Field Effect Transistor as Multi–Species Microprobe" in *Sensors and Actuators*, 4 (1983) 291–298.

J. A. Mihell et al., "Planar Thick–Film pH Electrodes Based on Ruthenium Dioxide Hydrate" in *Sensors and Actuators*, B 48 (1998) 505–511.

F. Oehme, "Liquid Electrolyte Sensors: Potentiometry, Amperometry, and Conductometry" in *Sensors—A Comprehensive Survey*, W. Göpel et al., Part I, VCM Publishers, 1991, pp. 239–339.

* cited by examiner

*Primary Examiner*—Nam Nguyen
*Assistant Examiner*—Kaj K. Olsen
(74) *Attorney, Agent, or Firm*—Dykema Gossett PLLC

(57) ABSTRACT

An electrochemical sensor includes an electrochemically active sensor layer (sensor spot), which is applied by means of thick film techniques in at least one region of an electrically insulating, planar substrate, the surface of the sensor layer being brought into contact in a measuring area with the aqueous sample to be determined. At least one conductive path for signal pick-up is also applied on the substrate by means of thick film techniques. The sensor layer contains at least one oxide of metal from subgroups 7 and 8 wof the Periodic Table as sensor component. The contact between the electrochemically active sensor layer and the conductor is effected via an electrically conductive bridge layer which extends from the measuring area in a direction essentially parallel to the surface of the substrate. The bridge layer consists of corrosion-resistant material.

30 Claims, 2 Drawing Sheets

ELECTROCHEMICAL SENSOR

BACKGROUND OF THE INVENTION

The present invention relates to an electrochemical sensor having in at least one region of an electrically insulating, planar substrate an electrochemically active sensor layer (sensor spot), which is applied by means of a thick film technique and the surface of which can be brought into contact in a measuring area with the aqueous sample to be determined, at least one conductive path being provided for signal pick-up which is also applied on the substrate by means of a thick film technique, and the sensor layer containing at least one oxide of a metal from subgroups 7 and 8 of the Periodic Table as sensor component.

DESCRIPTION OF THE PRIOR ART

In the following the term thick film techniques will include coating techniques such as screen printing, dispenser coating, tampon printing and similar such methods, where layer thicknesses of greater than 1 $\mu$m are obtained, whereas techniques such as vacuum depositing, sputtering, or photolithography, which are usually employed to obtain thicknesses of less than 500 nm, are considered as thin film techniques and will thus be excluded.

Due to their electrochemically active sensor layers the electrochemical sensors mentioned above, which may be operated amperometrically or potentiometrically, are primarily suitable for determining the pH value or $H_2O_2$ concentration, for example. By variations in the sensor configuration other quantities, which will influence or alter the pH or $H_2O_2$ concentration, may be determined in addition to these primary quantities. For example, a pH sensitive layer of a platinum metal oxide may be covered with a hydrophobic layer that is $CO_2$-permeable, and the $CO_2$ concentration may be determined from the resulting change in pH.

Incorporating $MnO_2$ into a suitable electrode material for anodic reaction of hydrogen peroxide also is standard practice. EP 0 603 154, for example, describes an amperometric enzyme electrode containing an enzyme immobilized or adsorbed in the porous electrode material. Depending on the concentration of the corresponding enzyme substrate in a sample there will be a variation in the concentration of hydrogen peroxide, which may be determined via the anodic reaction.

As regards the term "electrochemical sensor" to be used in the following it should be noted that this will essentially refer only to the electrochemically active base layer of the sensor and the elements picking up the electric signal. Any reference to further additives, or additional layers for transforming one chemical variable into another, is given only as an example without intending an exhaustive description. In the amperometric measuring process disclosed in EP 0 603 154, for instance, the enzyme need not necessarily be immobilized on the porous base electrode, as the enzymatic reaction could also take place outside of the sensor.

The pH sensitivity of the platinum metal oxides, which has been known in the art for some time, will permit the development of potentiometric pH sensors (or rather, sensors which are essentially based on pH measurement). Miniaturized planar sensors on the basis of metal oxide, which are intended for pH determination, are manufactured using thick film techniques, i.e. both conventional methods and, increasingly, polymer thick film processes.

DE 195 06 863 A1, for instance, discloses a pH sensor made by means of a thick film technique, and the corresponding manufacturing process. The sensor employs ruthenium oxide as an electrochemically active component, the layer containing the electrochemically active component being applied on a substrate using a polymer thick film technique. The individual layers are applied as following: First of all, a conductive path of silver is applied on the substrate, which is followed by the electrochemically active layer consisting of a mixture of ruthenium dioxide and a paste that is commonly used in polymer thick film technology for preparing insulating layers. In a final step, a non-conductive insulating layer is applied. The layers are tempered and cured in an oven.

In DE 44 30 662 A1 an iridium oxide electrode for pH measurement and a method of fabricating such an electrode are described. On a substrate of organic or inorganic material a pH sensitive layer is applied, which contains oxidized iridium powder. For preparation of the electrode iridium oxide powder is mixed with organic and/or inorganic binders; the resulting paste is applied to the substrate using a screen printing technique. The iridium pH electrodes obtained in this way are designed for pH measurement and as basic sensors for biosensors and gas sensors. The substrate consists of a ceramic material in this case, on which a conductive path is applied in a first printing step. In a second printing step the conductive path is covered with a polymer insulating layer with the exception of a contact area, which remains uncovered. In a third printing step the thick film paste containing iridium oxide is applied, after the addition of an intermediate layer if required.

With the metal oxide sensors known in the art the sequence of the printing steps is strictly prescribed, at least as far as the electrically conductive path and the metal oxide layer are concerned. This may be be undesirable, for example in the instance of cracks occurring at the interface of different materials, which may impair the conductivity and thus functionality of the sensor.

Another problem is due to the fact that electrochemically active sensor layers containing an oxide of the metals Mn, Ru, Ir, or Pt, exhibit a surface structure or contain a chemical substance which will permit the sample solution to penetrate the sensor layer and reach the conductor. This may lead to phenomena such as drifting (for example, due to swelling processes) and/or corrosion (forming of galvanic elements), as exemplified by the system based on ruthenium oxide and silver. Further negative effects are to be expected with working electrodes containing $MnO_2$ as electrochemically active component. Due to material swelling in the aqueous environment galvanic elements will be formed, which will impair the electrochemical characteristics of the sensor (distortion of the $H_2O_2$ signal, susceptibility to interferences, pH effects)

In "Sensors and Actuators" B 48, 1998, 505–511 the weakening of the pH signal during storage of a planar thick film pH electrode based on ruthenium dioxide is described in this context. Upon close examination of the storage conditions it becomes obvious that the sensor is being destroyed by corrosion. In the acid pH range (i.e. pH 2, approx.) ruthenium oxide has a standard potential of 0.86 V for the transition from Ru(IV) to Ru(III), and is thus capable of oxidizing silver, which will explain the corrosive destruction observed. As a possible solution to this problem use of a printed, spot-shaped intermediate layer is proposed between the electrochemically active sensor layer and the conductor. Apart from the disadvantage of an additional printing step, which will increase manufacturing costs, it has been found that such intermediate layers are susceptible to the diffusion of Ag ions after having been in use for some time (about 1 day), which will also impair the electrochemically active sensor layer.

Further interferences due to the diffusion of Ag ions have been found in sensors containing $MnO_2$ as sensor component for $H_2O_2$ detection. Such interferences include sudden short-term current flows produced by a discharge of the polarized, amperometric working electrodes acting as capacitors. In addition, longer polarization times are encountered on initial operation of the sensor, and a change in electrode behavior vis-a-vis electrochemical interferents such as uric acid or solutions with differing pH values is experienced throughout the service life of the electrode.

U.S. Pat. No. 5,507,936 shows a sensor configuration, where the electrochemically active sensor layer of iridium oxide is applied on a metal layer consisting of iridium, this metal layer providing the electrical connection to the conductor. The monocrystalline oxide layer may be produced in a high vacuum with the use of a thin-film technology and deposited on the carrier in one and the same working process. For this purpose a metallic iridium layer is formed in a first step of a vapor-deposition process. More iridium vapor is deposited on this layer in a second step directly following the first one, and oxygen is introduced at the same time. During the second step of the vapor-deposition process a monocrystalline layer of iridium oxide will form on the metallic support. Similarly, metal oxide layers of other metals from the seventh or eight subgroup of the Periodic Table may be formed. The oxide layer may have a surface coat of $IrO_2$ and a region consisting of $Ir_2O_3$ in the contact area with the metallic iridium layer.

Manufacture of such sensors is complex and expensive and does not permit the use of thick film techniques such as screen printing, dispenser printing or tampon printing. Similarly to the manufacture of ion-sensitive field effect transistors (ISFET) (see, for instance, EP 0 190 005 A2, or JP 01-112148A) expensive thin-film technologies must be employed, which will leave no scope for simple and inexpensive manufacturing methods.

In EP 0 651 248 A2, finally, a pH sensor is disclosed where a pH-sensitive metal oxide (such as ruthenium or iridium dioxide) is supported on a ceramic substrate, and where the signals are conducted to a solderable electric contact via a metal electrode consisting of platinum. The drawbacks of this system are the comparatively high costs due to the use of noble metals for the entire electrical path and the additional expense for providing a soldered connection.

SUMMARY OF THE INVENTION

It is an object of this invention to further develop electrochemical sensors as described above so that they can still be produced in a simple and inexpensive way using thick film techniques, whilst any interferences between conductive path and electrochemically active sensor layer are to be avoided.

According to the invention this object is achieved by providing that the contact between the electrochemically active sensor layer and the conductive path be effected via an electrically conductive bridge layer extending from the measuring area in a direction essentially in parallel with the surface of the substrate, which bridge layer should consist of corrosion-resistant material. In this manner the difficult transition from the electrochemically active sensor layer to the conductor is shifted into regions outside of the actual measuring area. This measuring area is generally defined by an opening in the cover coat or insulating layer of a planar sensor or by a sample channel through which the sample may be brought into contact with the sensitive region of the sensor layer. The bridge layer may thus lead away from the measuring area, or run beneath any wall bounding the measuring chamber or measuring channel, and will be brought into contact with the conductor only outside of the actual measuring area. The electrical contact between the sensor and the exterior is made by means of a clamped or plug-in connection at the conductor. As the printed layers are very thin (about 3 to 20 $\mu$m), any lateral diffusion of silver ions may be excluded, at least during the service life of the sensor. This is especially true for a ratio of length l to thickness d of the bridge layer greater 5, and preferably greater 50. The ratio between the length of the bridge layer and the diameter of the measuring area is between 1:1 and 10:1.

Preferably, a carbon conductor may be used for the bridge layer, whose conductivity is sufficient for the short distance of a few millimeters. The conductive path may be made of conventional materials, such as silver or copper. The use of carbon for the entire length of the conductive path is not commendable, as carbon conductors have a resistance of 0.5 to several 1000 k$\Omega$/cm, so that their conductivity would not suffice for amperometric uses.

The short bridge layer could also consist of a noble metal, such as Au or Pt, or could contain a noble metal, as material costs for such a comparatively small part of the conductor could be kept low.

The bridge between the electrochemically active sensor layer and the conductive path could also be provided in the form of an electrolyte bridge, which is provided with an electrically insulating cover.

It is provided in an especially advantageous variant of the invention that the bridge layer consist of the material of the electrochemically active sensor layer, and that it be preferably applied on the substrate together with the sensor layer in one and the same processing step. In this preferred variant the material of the electrochemically active sensor layer extends beyond the actual measuring window and forms at least part of the electrical conductor. Contact with the conductive path of silver or gold is established outside of the region in which negative influences could be exerted by the sample. The electrochemically active sensor layer lends itself as a bridge layer above all in conjunction with layers containing ruthenium oxide, which exhibit very low resistances (only about 100 $\Omega$). Among the advantages of this variant are the small number of printing steps and materials required.

In a variant offering particularly desirable electrochemical properties it is provided that the electrochemically active sensor layer contain at least one oxide of the metals of subgroup 8 of the Periodic Table, i.e. preferably $RuO_2$, and organic polymers for bonding, i.e. preferably polyvinyl acetate, polyurethane, or epoxy resins.

Example of an Electrochemically Active Sensor Layer Containing $RuO_2$

Ruthenium oxide and insulating paste are mixed in a ratio of between 1:2 and 2:1 parts by weight, rolled with a three-roll mill, and printed by means of a screen-printer on a planar substrate made of ceramic, plastic, or printed circuit board material (preferably $Al_2O_3$ or polycarbonate), and temper-hardened. In an advantageous application, a commercially available preparation containing ruthenium oxide may be used, which is made by GEM Ltd, Pontypool, UK, and features great ease of processing. Conductive path and insulating layer are printed in the same manner known to those skilled in the art.

In a low-cost variant of an amperometric $H_2O_2$ sensor it is provided that the electrochemically active sensor layer have an oxide of the metals of subgroup 7 of the Periodic Table, preferably $MnO_2$, incorporated in a paste containing carbon, such as graphite or activated charcoal, and organic polymers for bonding, preferably polyvinyl acetate, polyurethane, or epoxy resins.

Example of an Electrochemically Active Sensor Layer Containing $MnO_2$

Onto a plastic support silver conductors are printed for the reference electrode, counterelectrode and the enzyme working electrode. For preparation of the reference electrode an Ag/AgCl paste is used, at least in the sensor region. The counterelectrodes are coated with a carbon paste in the sensor region. During the same step of the manufacturing process the bridge layer is fabricated from the carbon paste used for the working electrode. The working electrode is dispenser-coated onto the sensor area from a mixture of 5% manganese dioxide in a carbon paste. In a next step, the entire system, with the exception of the electrode spots designed for contact with the sample fluid and the conductor ends designed for signal pick-up, is coated with an insulating varnish. The sensor may thus be used for determination of hydrogen peroxide, or, in an extended variant, as an enzyme electrode. For this purpose one drop of a 10% solution of glucose oxidase (or, alternatively, a 2.5% solution of lactate oxidase) in water is applied; alternatively, a matrix of self-curing polyacrylate may be used. In a final step a cover membrane consisting of a polymer solution may be applied.

As an alternative, the base sensor may be coated with an interference barrier membrane as described in the relevant literature.

Suitable materials for fabrication of the bridge layer are carbon paste, gold, platinum, or the material used for the working electrode ($MnO_2$ in carbon paste)

BRIEF DESCRIPTION OF THE DRAWINGS

The invention will be better understood by reference to the attached drawings.

DETAILED DESCRIPTION OF THE PREFERRED EMBODIMENTS

Please note that the thicknesses of the individual layers, which are between 5 and 40 $\mu$m only, are strongly exaggerated in all Figures.

Figure 1:
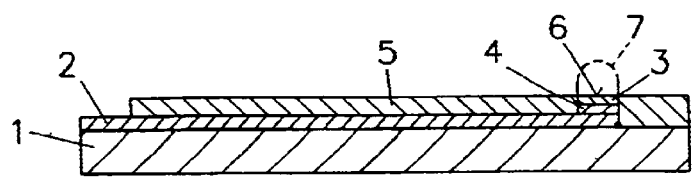
FIG. 1 shows a sectional view through an electrochemical sensor according to the prior art.

The state-of-the-art sensor shown in FIG. 1 has a planar, electrically insulating substrate 1, on which is printed by means of a thick film technique (see above) a conductive path or conductor 2 consisting of silver, for example. At one end of the conductor 2 is provided the electrochemically active sensor layer 3 configured as a sensor spot. If desired, an intermediate layer 4 may be provided between the conductor 2 and the sensor layer 3. 5 refers to an electrically insulating cover layer; the measuring area 6 of the electrochemically active sensor layer 3 remains uncovered. A measuring chamber or measuring channel 7 is indicated by a broken line. The conductors of existing electrochemical sensors are usually made of silver, which means that the silver ions may easily diffuse into the electrochemically active sensor layer 3 directly on top of the conductor or separated from it by a thin intermediate layer 4 only, and will lead to the above described disadvantages.

In the variants according to the invention, which are shown in FIGS. 2 to 5, contact between the electrochemically active sensor layer 3 and the conductive path 2 is effected via an electrically conductive bridge layer 8 departing from the measuring area 6 essentially in parallel with the surface of the substrate, which layer 8 consists of corrosion-resistant material. The ratio of the length l of the bridge layer 8 to its thickness d is >5, and preferably >50 (see FIG. 2).

Figure 2:
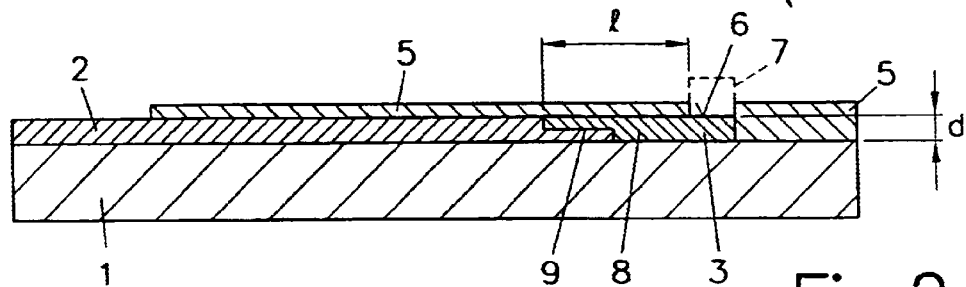
FIG. 2 shows a sectional view through an electrochemical sensor according to a first preferred embodiment of the present invention.
Figure 3:
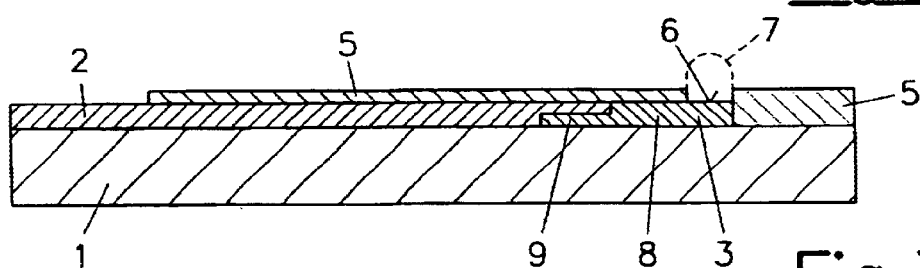
FIG. 3 shows a sectional view through an electrochemical sensor according to a second preferred embodiment of the present invention.

In the variants according to FIGS. 2 and 3 the bridge layer 8 consists of the same material as the electrochemically active sensor layer 3 and may thus be applied on the substrate 1 together with the sensor layer in a single processing step. For improved contact the bridge layer 8 and the conductor 2 may overlap in their contact region 9. The variants of FIGS. 2 and 3 offer the additional advantage that the electrically active sensor layer 3 and the electric conductor 2 may be applied by thick film techniques in any sequence desired, or rather, the printing sequence may be varied between conductor 2 and electrochemically active sensor layer 3. For example, the sensor layer 3 could be printed before the conductor 2. In a special case this would allow the use of pastes which could otherwise not be employed due to their tendency of cracking.

Figure 4:
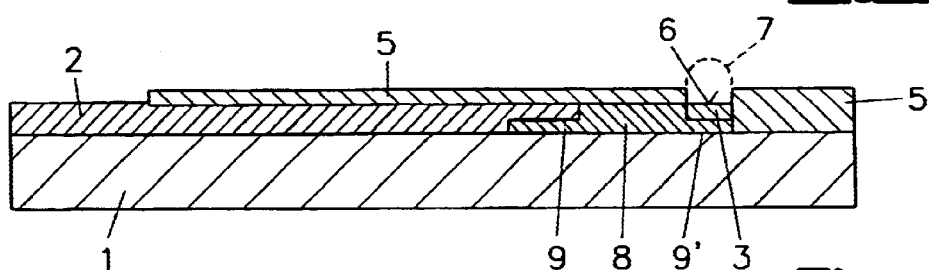
FIG. 4 shows a sectional view through an electrochemical sensor according to a third preferred embodiment of the present invention.

In the variant according to FIG. 4 an electrolyte bridge is provided between the electrochemically active sensor layer 3 and the conductor 2 as a bridge layer 8, which forms overlap regions 9, 9' with the conductor 2 and the electrochemically active layer 3.

Figure 5:
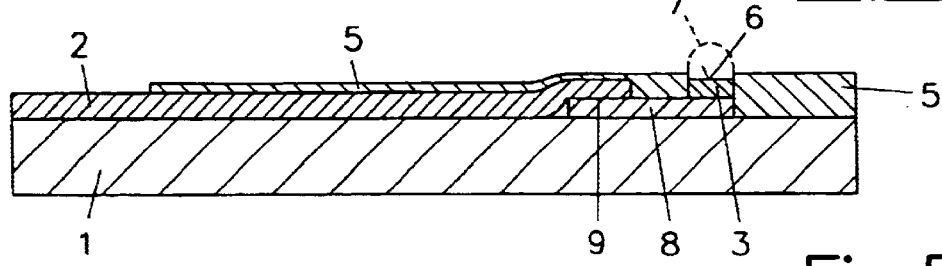
FIG. 5 shows a sectional view through an electrochemical sensor according to a fourth preferred embodiment of the present invention.

In the variant of FIG. 5 the bridge layer consists of carbon, for example, whose electrical conductivity will suffice for the relatively short distance of 1 to 2 mm between the sensor spot 3 applied on one end of the bridge layer 8 and the conductor 2. It would also be possible in this variant to provide a bridge layer consisting of a noble metal, such as gold or platinum, as the shortness of the bridge elements would permit material costs to be kept reasonably low.

Figure 6:
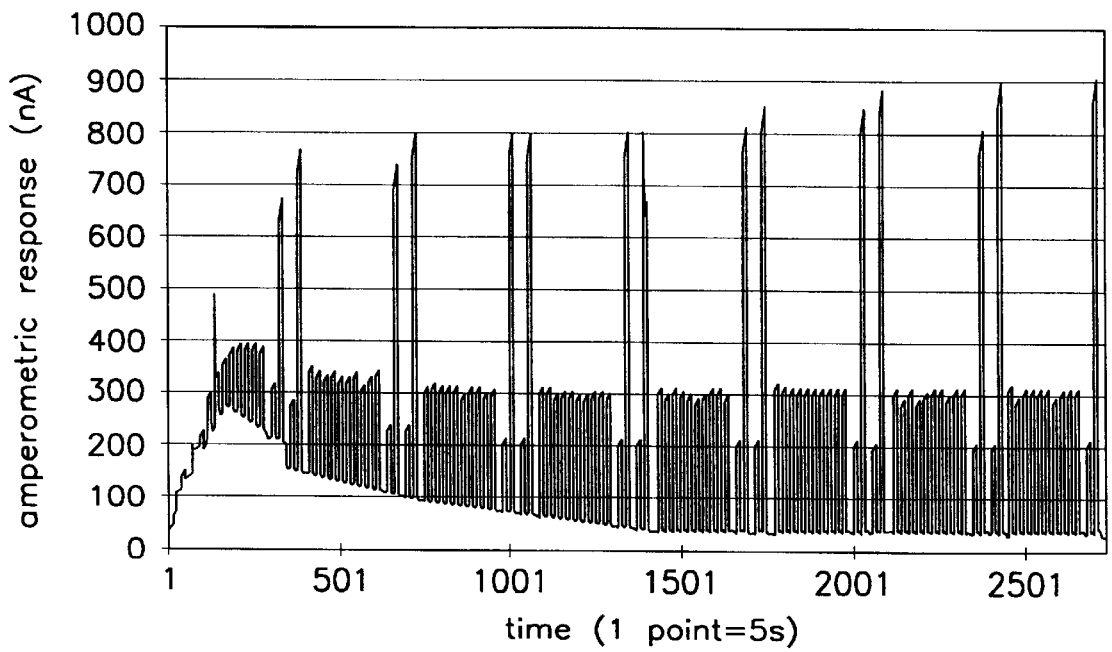
FIGS. 6 and 7 show polarization curves of electrochemical sensors which exclude (FIG. 6) or include (FIG. 7) bridge layers.
Figure 7:
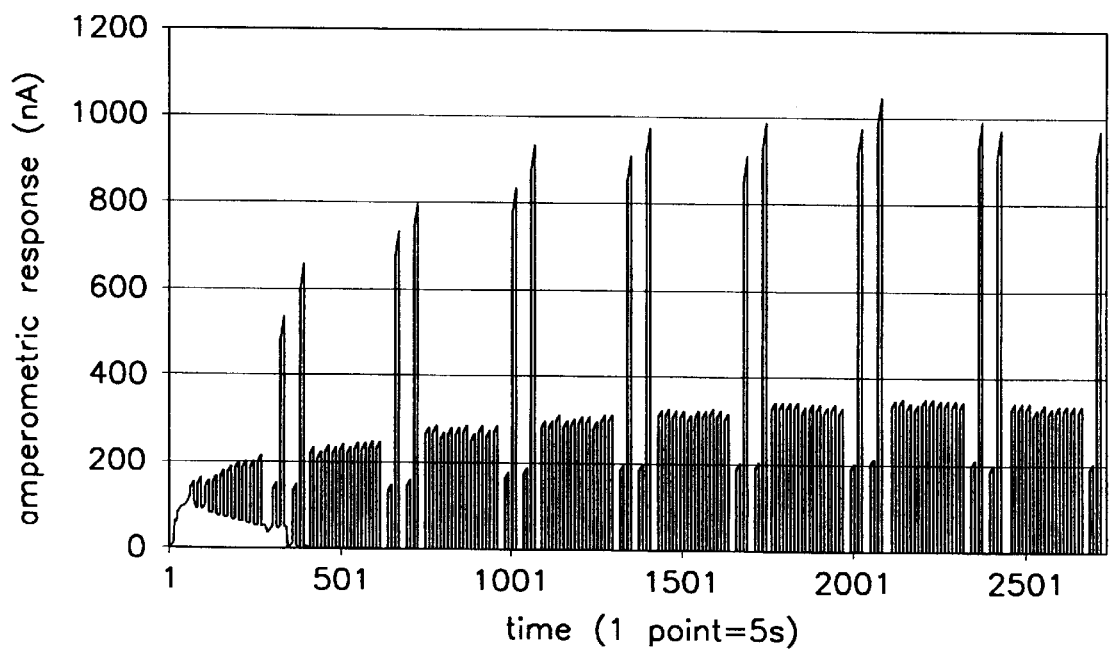

FIGS. 6 and 7 show differences in the polarization curves of amperometric $MnO_2$ sensors for determination of hydrogen peroxide with the additional use of an immobilized enzyme, such as glucose oxidase, which do or do not include the bridge layer according to the invention. FIG. 6 shows the polarization curve over time of a sensor with a conductor made of Ag/AgCl paste and extending directly below the working electrode. The polarization curve shown in FIG. 6 shows both zero current and operating current of the sensor for sample measurements alternating between 5 mM glucose, 25 mM glucose, 10 samples of cattle serum, 5 mM glucose and 25 mM glucose.

Each of these samples is rinsed off with a glucose-free solution and the zero current is measured as a base value. In the time span shown in FIGS. 6 and 7 a total of 8 such cycles are passed through, corresponding to an overall measurement time of about 4 hours. FIG. 7 shows the polarization curve of an electrode of the same configuration as above, but additionally including a bridge layer of carbon paste as described by the invention. The measuring cycle corresponds to the one in FIG. 6. It is clearly seen that the bridge layer results in a shorter polarization phase (time span until a small, constant zero current is obtained) in addition to significantly reducing the amplitude of the polarization current. With the use of a bridge layer, for instance, the zero current will drop to a level of 0 nA within 30 minutes or less, whereas a zero current of about 35 nA will prevail even after a time lapse of 4 hours in the absence of a bridge layer.

In all variants according to the invention the conductive path 2 consisting of silver or copper is separated from the sensor spot 3 by a bridge layer 8, which will efficiently prevent interfering ions from diffusing into the sensor layer, or any negative effects due to galvanic elements.

We claim:

1. An electrochemical sensor comprising:
   an electrically insulating, planar substrate having a planar surface,
   an electrochemically active sensor layer, which is applied by means of thick film techniques in at least one region of said planar substrate, said sensor layer containing at least one oxide of a metal belonging to one of the subgroups 7 and 8 of the Periodic Table of chemical elements as sensor component, and contacting in a measuring area an aqueous sample to be determined,
   at least one conductive path for signal pick-up which is applied on said planar substrate by means of thick film techniques and which is located entirely outside of said measuring area, and wherein said electrochemically active sensor layer extends from said measuring area as an electrically conductive bridge layer in a direction essentially in parallel with said planar surface of said substrate and outside said measuring area to contact said conductive path, wherein said bridge layer is electrically insulated and wherein a ratio of length l of said bridge layer outside of said measuring area to thickness d thereof is greater than 5.

2. A sensor as claimed in claim 1, wherein said electrically active sensor layer and said conductive path are applied by thick film techniques in any sequence desired.

3. A sensor as claimed in claim 1, wherein said bridge layer is applied on said planar substrate together with said sensor layer in one processing step.

4. A sensor as claimed in claim 1, wherein a ratio of length l to thickness d of said bridge layer is greater than 50.

5. A sensor as claimed in claim 1, wherein a ratio between the length l of said bridge layer and a diameter of said measuring area is between 1:1 and 10:1.

6. A sensor as claimed in claim 1, wherein said bridge layer and said conductive path overlap in a contact region.

7. A sensor as claimed in claim 1, wherein said at least one oxide of a metal of said electrochemically active sensor layer belongs to subgroup 8 of the Periodic Table of chemical elements, and wherein said sensor layer contains an organic polymer for bonding.

8. A sensor as claimed in claim 7, wherein said oxide of a metal is $RuO_2$ and said organic polymer is selected from the group consisting of polyvinyl acetate, polyurethane and epoxy resins.

9. A sensor as claimed in claim 1, wherein said at least one oxide of a metal of said electrochemically active sensor layer belongs to subgroup 7 of the Periodic Table of chemical elements and is incorporated in a paste containing carbon and an organic polymer for bonding.

10. A sensor as claimed in claim 9, wherein said carbon is graphite or activated charcoal.

11. A sensor as claimed in claim 9, wherein said organic polymer is selected from the group consisting of polyvinyl acetate, polyurethane and epoxy resins.

12. A sensor according to claim 1, including at least one additional layer contacting said electrochemically active sensor-layer.

13. A sensor according to claim 12, wherein said additional layer comprises glucose oxidase or lactate oxidase.

14. A sensor according to claim 12, wherein said additional layer is a hydrophobic, $CO_2$-permeable layer.

15. An electrochemical sensor comprising:
    an electrically insulating, planar substrate having a planar surface,
    an electrochemically active sensor layer, which is applied by means of thick film techniques in at least one region of said planar substrate, said sensor layer containing at least one oxide of a metal belonging to one of the subgroups 7 and 8 of the Periodic Table of chemical elements as sensor component, and contacting in a measuring area an aqueous sample to be determined,
    at least one conductive path being provided for signal pickup, which is also applied on said planar substrate by means of thick film techniques and which is located entirely outside of said measuring area,
    wherein said electrochemically active sensor layer contacts an electrically conductive bridge layer extending from said measuring area in a direction essentially in parallel with said surface of said planar substrate and outside said measuring area to said conductive path, wherein said bridge layer consists of corrosion resistant material and wherein a ratio of length l of said bridge layer outside of said measuring area to thickness d thereof is greater than 5.

16. A sensor as claimed in claim 15, wherein said bridge layer consists of carbon.

17. A sensor as claimed in claim 15, wherein said bridge layer is an electrolyte bridge.

18. A sensor as claimed in claim 15, wherein said bridge layer consists of a noble metal or contains a noble metal.

19. A sensor as claimed in claim 15, wherein said electrochemically active sensor layer is applied on one end of said bridge layer.

20. A sensor as claimed in claim 15, wherein a ratio of length l to thickness d of said bridge layer is greater than 50.

21. A sensor as claimed in claim 15, wherein a ratio between the length l of said bridge layer and he a diameter of said measuring area is between 1:1 and 10:1.

22. A sensor as claimed in claim 15, wherein said bridge layer and said conductive path overlap in a contact region.

23. A sensor as claimed in claim 15, wherein said at least one oxide of a metal of said electrochemically active sensor layer belongs to subgroup 8 of the Periodic Table of chemical elements and wherein said sensor layer contains an organic polymer for bonding.

24. A sensor as claimed in claim 23, wherein said oxide of a metal is $RuO_2$ and said organic polymer is selected from the group consisting of polyvinyl acetate, polyurethane and epoxy resins.

25. A sensor as claimed in claim 15 wherein said at least one oxide of a metal of said electrochemically active sensor layer belongs to subgroup 7 of the Periodic Table of chemical elements and is incorporated in a paste containing carbon and an organic polymer for bonding.

26. A sensor as claimed in claim 25, wherein said carbon paste contains graphite or activated charcoal.

27. A sensor as claimed in claim 25, wherein said organic polymer is selected from the group consisting of polyvinyl acetate, polyurethane and epoxy resins.

28. A sensor according to claim 15, including at least one additional layer contacting said electrochemically active sensor layer.

29. A sensor according to claim 28, wherein said additional layer comprises glucose oxidase or lactate oxidase.

30. A sensor according to claim 28, wherein said additional layer is hydrophobic, $CO_2$-permeable layer.

* * * * *